United States Patent [19]
Morrison

[11] Patent Number: 4,719,101
[45] Date of Patent: Jan. 12, 1988

[54] DEODORANT COMPOSITION TO PROTECT AGAINST THE DEVELOPMENT OF BODY ODOR

[76] Inventor: Keith Morrison, 2970 Pasadena, Detroit, Mich. 48238

[21] Appl. No.: 935,921

[22] Filed: Nov. 28, 1986

[51] Int. Cl.$^4$ .............................................. A61K 7/32
[52] U.S. Cl. ........................................ 424/65; 514/969
[58] Field of Search ........................... 424/65; 514/969

[56] References Cited

U.S. PATENT DOCUMENTS

| | | | |
|---|---|---|---|
| 1,219,451 | 3/1917 | Gardos | 424/65 |
| 1,545,931 | 7/1925 | Weeks | 424/65 |
| 2,246,524 | 6/1941 | Kyrides | 424/65 |
| 2,294,140 | 8/1942 | Taylor | 424/65 |
| 3,091,511 | 5/1963 | Calhoun | 424/65 |
| 4,450,151 | 5/1984 | Shinozawa | 514/179 |
| 4,457,910 | 7/1984 | Van Cleave | 514/179 |

OTHER PUBLICATIONS

The Merck Index, 9th edition, 1976, pp., 219, 220, 510 and 798.
Martindale, The Extra Pharmacopoeia, 24th edition, 1958, vol. I, pp. 1180 to 1182.

*Primary Examiner*—Dale R. Ore
*Attorney, Agent, or Firm*—Brooks & Kushman

[57] ABSTRACT

A deodorant composition comprises a cosmetically acceptable vehicle containing methyl salicylate and a solubility enhancing oil, preferably peanut oil. The composition is externally applied to the skin, generally to the feet of the user, and provides protection against development of odor.

3 Claims, No Drawings

DEODORANT COMPOSITION TO PROTECT AGAINST THE DEVELOPMENT OF BODY ODOR

TECHNICAL FIELD

This invention relates to a cream deodorant composition containing methyl salicylate as the surface active agent.

BACKGROUND OF THE INVENTION

Odor from a human body constitutes a problem. It has long been recognized that certain chemical compositions will prevent human body odor without adversely affecting the health of the applicant. Foot odor has presented a particularly severe problem, and many attempts have been made to solve it.

Traditionally, sprays, powders, and other deodorant application have attempted to eliminate foot odor. Sprays and powders have left residual particles on the feet of the consumer, thereby causing a maintenance problem within the socks and shoes. Other products have met with similar unsuccessful results.

U.S. Pat. No. 4,278,658 issued on July 14, 1981 to Hooper, et al., in which a deodorant composition is described for application to regions of the human body where apocrine sweat glands are located, such as in the groin, axilla, anal and genital regions and in the aureola of the nipple. Described therein is a deodorant composition containing at least five components, including phenolic substances in combination with oils, aldehydes and ketones, polycyclic compounds, esters and alcohols.

SUMMARY OF THE INVENTION

A deodorant composition comprises a cosmetically acceptable vehicle for the deodorant composition, methyl salicylate as the surface active agent, and a solubility enhancing oil in sufficient amounts to dissolve the methyl salicylate into the composition vehicle. Further components are included for emulsification, fragrance, preservation, and for the enhancement of its general properties. This composition results in a deodorant cream easily applicable to feet.

The composition of the deodorant includes the following constituents: from about 0.01 to about 0.10 percent by weight of methyl salicylate, up to 99.9 percent by weight of a cosmetically acceptable vehicle for the composition, and a solubility enhancing oil in sufficient amounts to dissolve the methyl salicylate into the composition vehicle.

An object of the present invention is to provide an improved deodorant composition for the topical application to the foot of a consumer. This deodorant composition may include a cosmetically acceptable vehicle, such as water, in combination with glycerine, oleyl alcohol, stearic acid, lanolin, peanut oil, polyethylene glycol stearate, dimethicone, triethanolamine, polyethylene ether, methyl salicylate, propylparaben, methylparaben and fragrances and colorings.

DESCRIPTION OF THE INVENTION

The present invention is directed to a cream deodorant composition useful in the prevention of foot odor in consumers. The composition includes a commercially acceptable vehicle, such as water, combined with glycerine and a deodorant composition containing methyl salicylate dissolved in a solubility enhancing oil, such as peanut oil.

Preferably, the composition contains methyl salicylate and up to 80% water, up to 15% glycerine, up to 10% oleyl alcohol, up to 10% stearic acid, up to 5% polawax, up to 5% lanolin, and up to 5% peanut oil. These percentages are expressed in percentage by weight. Methyl salicylate is preferably present between 0.01% by weight 0.10% by weight.

Methyl salicylate, commonly referred to as oil of wintergreen, is the surface-active agent in creams prepared in accordance with the present invention. The U.S. Food and Drug Administration requires compliance with FDA regulations if the concentration of methyl salicylate is greater than 0.10 percentage by weight. However, the preferred concentration for topical applications is up to 0.10 percentages by weight.

Peanut oil is added in amounts from about 0.5% and 5% by weight to aid the solubility of the methyl salicylate into the vehicle. Peanut oil is the preferred solubility enhancing oil because the methyl salicylate completely dissolves in its presence, while maintaining the neutrality of the fragrance of the cream composition. Other oils alter the fragrance in a disadvantageous manner, rendering the preparation unpleasant to use. Creams prepared according to the present invention have a mild, minty odor, both pleasant and effective.

In the examples described hereinbelow, the amounts are given in percentages by weight. Illustrative compositions of the present invention are disclosed, but the examples are not meant to limit the invention in any manner.

EXAMPLE 1

A cream deodorant composition was prepared with the following constituents:

|  | Percentage by Weight |
| --- | --- |
| Water | 71.00 |
| Glycerine | 10.00 |
| Oleyl Alcohol | 5.00 |
| Stearic Acid | 3.00 |
| Polawax | 3.00 |
| Lanolin | 3.00 |
| Peanut Oil | 2.00 |
| PEG-50 | 1.00 |
| Dimethicone | 1.00 |
| Triethanolamine | 1.00 |
| Laneth-15 | .60 |
| Methyl Salicylate | .10 |
| Propylparaben | .10 |
| Methylparaben | .10 |
| Camphor | .05 |
| D&C Red #19 | trace |
| Fragrance | trace |

The methyl salicylate and the other oil soluble ingredients were dissolved into the peanut oil before dissolution into the vehicle. The glycerine and oleyl alcohol were mixed with the water and then all ingredients were combined to form the deodorant cream. Upon testing on human feet, the cream was effective in reducing odor.

EXAMPLE 2

A cream deodorant composition was prepared with the following constituents:

| | Percentage by Weight |
|---|---|
| Water | 77.75 |
| Stearic Acid | 3.00 |
| Propylene Glycol | 3.00 |
| Glyceryl Stearate | 2.00 |
| Sorbitol | 2.00 |
| Polyethylene Laureth-4 | 2.00 |
| Peanut Oil | 2.00 |
| Isopropyl Palmitate | 1.00 |
| Dimethicone | 1.00 |
| Hydrolyzed Animal Protein | 1.00 |
| Methylparaben | 1.00 |
| Imidazolidinyl Urea | 1.00 |
| PEG-8 | 1.00 |
| PEG-12 | 1.00 |
| Quaternium-15 | 0.60 |
| Eucalyptus Oil | 0.50 |
| Methyl Salicylate | 0.10 |
| Camphor | 0.05 |
| Red No. 33 | trace |
| Fragrance | trace |

Once again, the methyl salicylate and the other oil soluble ingredients were dissolved into heated peanut oil before dissolution into the vehicle. The other constituents were mixed with the water and all ingredients were combined to form the deodorant cream. Upon testing on human feet, this composition was effective in reducing odor.

While the best modes have been described in detail, those familiar with the art to which this invention relates will recognize various alternative compositions and methods for practicing the invention as defined by the following claims.

What is claimed is:

1. A deodorant composition, comprising:
from about 0.01 to 0.10 percent by weight of methyl salicylate;
from about 70 to 75 percent by weight of water;
from about 1 to 10 percent by weight of oleyl alcohol;
from about 1 to 10 percent by weight of stearic acid;
from about 1 to 5 percent by weight of lanolin; and
a sufficient amount of peanut oil to dissolve the methyl salicylate into the composition, said composition forming a cream for external application.

2. A deodorant composition, comprising:

| | Percentage by Weight |
|---|---|
| Water | 71.00 |
| Glycerine | 10.00 |
| Oleyl Alcohol | 5.00 |
| Stearic Acid | 3.00 |
| Polawax | 3.00 |
| Lanolin | 3.00 |
| Peanut Oil | 2.00 |
| PEG-50 | 1.00 |
| Dimethicone | 1.00 |
| Triethanolamine | 1.00 |
| Laneth-15 | .60 |
| Methyl Salicylate | .10 |
| Propylparaben | .10 |
| Methylparaben | .10 |
| Camphor | .05 |
| D&C Red #19 | trace |
| Fragrance | trace |

3. A deodorant composition, comprising:

| | Percentage by Weight |
|---|---|
| Water | 77.75 |
| Stearic Acid | 3.00 |
| Propylene Glycol | 3.00 |
| Glyceryl Stearate | 2.00 |
| Sorbitol | 2.00 |
| Polyethylene Laureth-4 | 2.00 |
| Peanut Oil | 2.00 |
| Isopropyl Palmitate | 1.00 |
| Dimethicone | 1.00 |
| Hydrolyzed Animal Protein | 1.00 |
| Methylparaben | 1.00 |
| Imidazolidinyl Urea | 1.00 |
| PEG-8 | 1.00 |
| PEG-12 | 1.00 |
| Quaternium-15 | 0.60 |
| Eucalyptus Oil | 0.50 |
| Methyl Salicylate | 0.10 |
| Camphor | 0.05 |
| Red No. 33 | trace |
| Fragrance | trace. |

* * * * *